US008567738B1

(12) United States Patent
Adair

(10) Patent No.: US 8,567,738 B1
(45) Date of Patent: Oct. 29, 2013

(54) PORTABLE INTRAVENOUS DEVICE AND HANGER THEREFOR

(76) Inventor: James Adair, Georgetown, KY (US)

(*) Notice: Subject to any disclaimer, the term of this patent is extended or adjusted under 35 U.S.C. 154(b) by 0 days.

(21) Appl. No.: 13/346,908

(22) Filed: Jan. 10, 2012

(51) Int. Cl.
A47H 1/10 (2006.01)
F16M 11/00 (2006.01)
F16M 13/00 (2006.01)
A47F 1/14 (2006.01)
A47F 7/14 (2006.01)
A47F 5/08 (2006.01)
A47B 43/00 (2006.01)
A61F 5/37 (2006.01)

(52) U.S. Cl.
USPC ........... 248/328; 248/200; 248/201; 248/470; 248/475.1; 248/580; 128/877; 211/117; 211/118; 211/209

(58) Field of Classification Search
CPC ....... F16M 13/02; F16M 11/10; F16M 13/00; B60R 11/06; G09F 7/18
USPC ......... 248/328, 329, 332, 300, 301, 303, 215; 211/118, 115, 119.004, 209, 208; 602/32–39; 604/257, 262, 408–410, 80
IPC ...................... F16L 3/00; E04G 3/08
See application file for complete search history.

(56) References Cited

U.S. PATENT DOCUMENTS

| 1,575,177 | A | * | 3/1926 | Moran | 248/328 |
|---|---|---|---|---|---|
| 1,633,344 | A | * | 6/1927 | Moran | 248/328 |
| 2,954,028 | A | * | 9/1960 | Smith | 604/80 |
| 3,784,145 | A | | 1/1974 | Lawrie | |
| 3,924,781 | A | * | 12/1975 | Witte | 222/80 |
| 4,220,306 | A | * | 9/1980 | Cueto et al. | 248/328 |
| 4,699,613 | A | * | 10/1987 | Donawick et al. | 604/80 |
| 4,872,632 | A | | 10/1989 | Johnson | |
| 5,067,621 | A | * | 11/1991 | Alexander | 211/117 |
| 5,865,797 | A | * | 2/1999 | Zeeman | 604/80 |
| 6,015,371 | A | * | 1/2000 | Davitt | 482/129 |
| 6,061,989 | A | * | 5/2000 | Trivedi et al. | 52/633 |
| 6,182,662 | B1 | * | 2/2001 | McGhee | 128/845 |
| 6,290,192 | B1 | * | 9/2001 | Messerli | 248/188.5 |
| 7,325,778 | B2 | * | 2/2008 | Kuhn | 248/327 |
| 2004/0222341 | A1 | | 11/2004 | Breda et al. | |
| 2005/0017142 | A1 | * | 1/2005 | Ogden | 248/247 |
| 2008/0135711 | A1 | * | 6/2008 | Bunting | 248/328 |

* cited by examiner

Primary Examiner — Daniel J Troy
Assistant Examiner — Muhammad Ijaz
(74) Attorney, Agent, or Firm — Montgomery Patent & Design; Robert C. Montgomery

(57) ABSTRACT

An IV hanger providing a portable adjustable hanging attachment for conventional intravenous equipment comprises an attachment method, a pulley system, and a hanging bracket. The attachment method comprises a plurality of attachment means for attaching the apparatus to an elevated structure. The attachment method is integrally connected to a pulley system which allows a user to selectively adjust the height of the hanging bracket relative to the frame. The hanging bracket provides a plurality of attachment hooks for support of IV equipment. The apparatus is particularly adapted for veterinary field calls where ground-based support system are prone to damage or disturbance by animal patients.

16 Claims, 14 Drawing Sheets

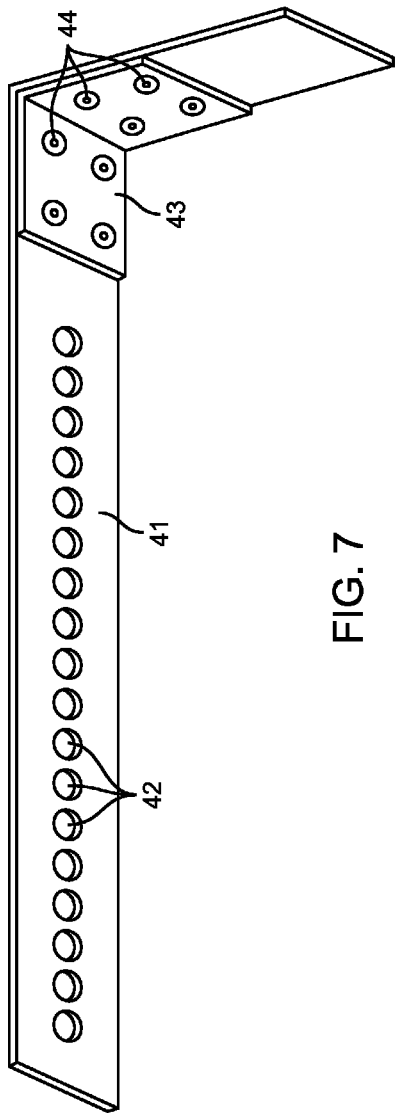
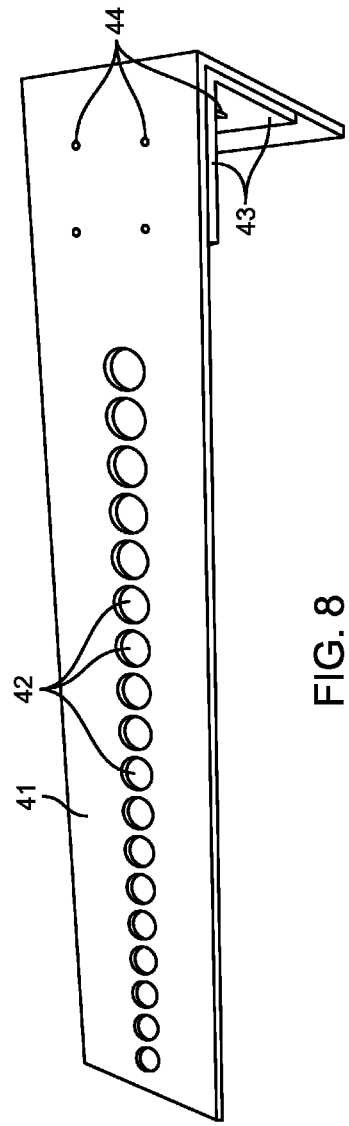
FIG. 7
FIG. 8

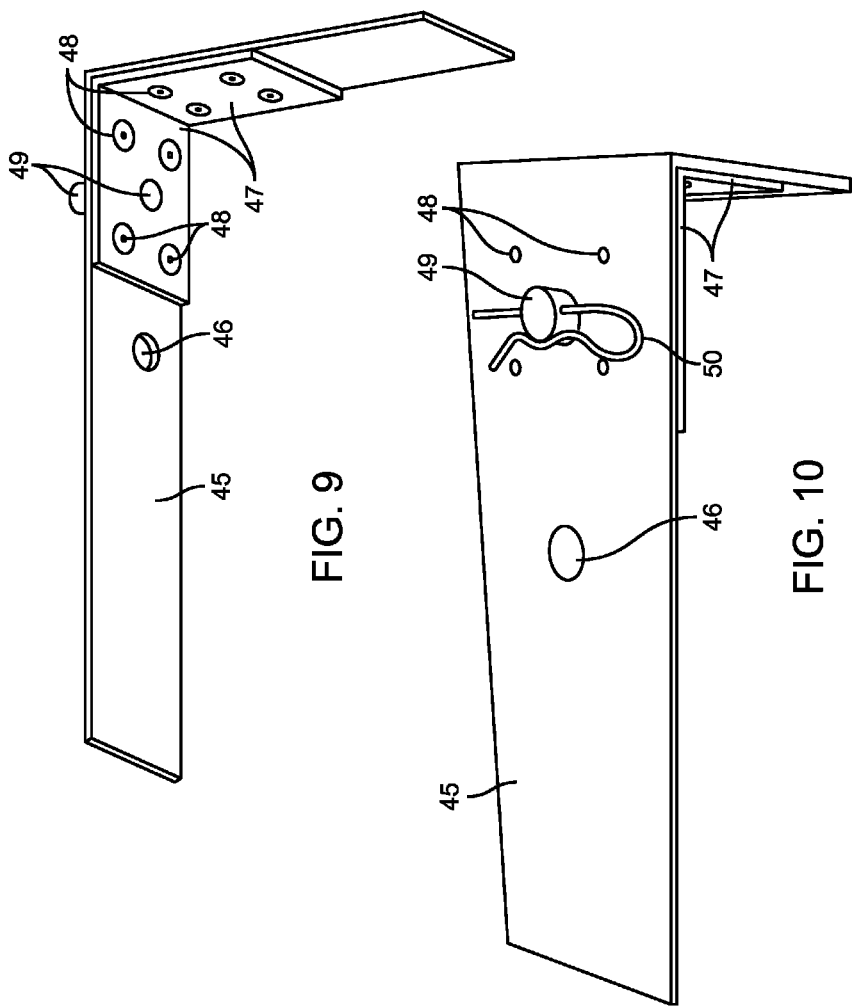

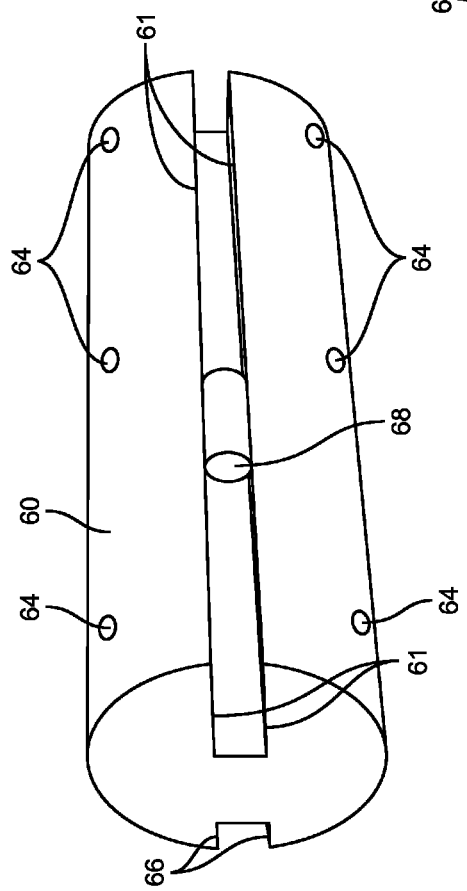
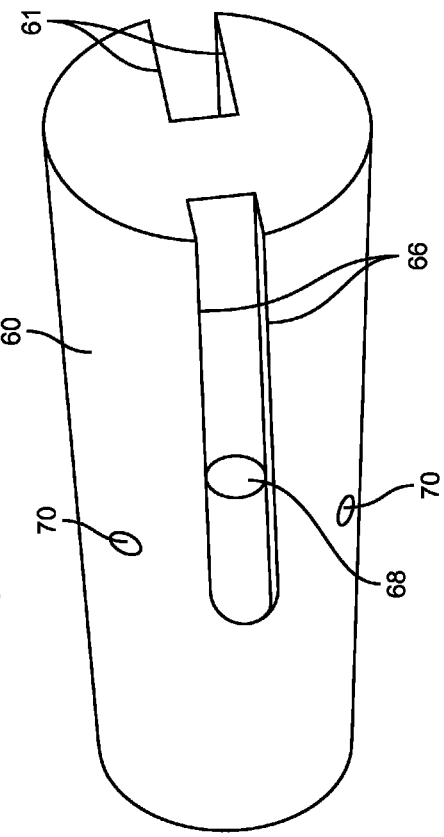

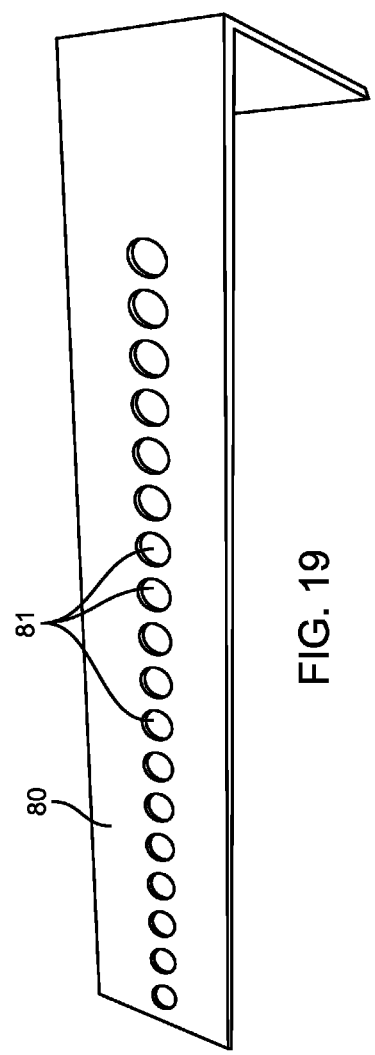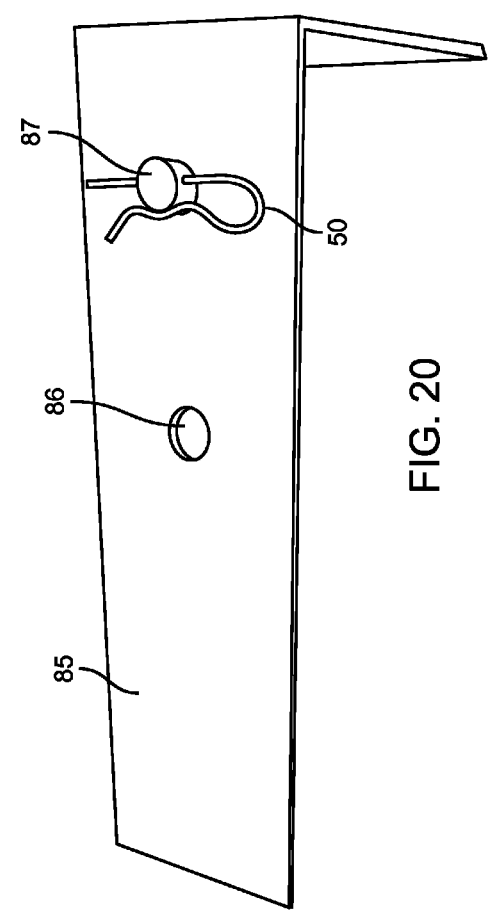

US 8,567,738 B1

PORTABLE INTRAVENOUS DEVICE AND HANGER THEREFOR

RELATED APPLICATIONS

There are currently no applications co-pending with the present application.

FIELD OF THE INVENTION

The present invention relates generally to supports for intravenous equipment, and in particular, to intravenous bags and lines administered to animals.

BACKGROUND OF THE INVENTION

Many animals require intravenous treatments or medications which further require appropriate equipment to suspend the treatment while in use. Placing the intravenous equipment on a ground surface is an irresponsible choice when dealing with the unpredictable characteristics of animals. Also many stalls or similar accommodations for animals are cramped and lacking of sufficient elevated support options. Various ways to suspend intravenous are known. They include makeshift structures and persons retaining intravenous equipment during treatments; each of which retains intravenous equipment.

Various attempts have been made to provide portable IV hangers. Examples of these attempts can be seen by reference to several U.S. Patent No. 2004/0,222,341, issued in the name of Breda et al., describes an intravenous infusing equipment hanger assembly comprising a mounting plate for attachment onto a wall.

U.S. Pat. No. 3,784,145, issued in the name of Lawrie, describes an adjustable intravenous bottle pendant assembly.

U.S. Pat. No. 4,872,632, issued in the name of Johnson, describes an apparatus for suspending articles overhead.

While these attempts may fulfill their respective, particular objectives, each of these references suffer from one (1) or more disadvantages. Many are not suited to provide adequate suspension to intravenous equipment. Others are limited and provide a permanent suspension to items.

SUMMARY OF THE INVENTION

The inventor has recognized the aforementioned inherent problems and lack in the art and observed that there is a need for a portable intravenous (IV) hanger which accommodates temporarily suspending intravenous equipment for administering treatments and medicines to animals.

Accordingly, it is an object of the present embodiments of the invention to solve at least one of these problems. The inventor has addressed this need by developing portable IV hanger that provides suspension to intravenous treatment bags and medicines.

To achieve the above objectives, it is an object of the present invention to administer medications intravenously to animals and enable an IV bag to be adjustably suspended which prevents accidental toppling and appropriate injection of the medication into the animal.

Another object of the present invention is to provide an upper retaining member fixed to an upper pulley to enable a desired adjustable suspension to the apparatus.

Yet still another object of the present invention is to provide an adjustable bracket attachment which enables placement upon doorways or other horizontal structures.

Yet still another object of the present invention is to provide hook attachment to provide placement to hooks or other vertical members.

Yet still another object of the present invention is to provide a lower retaining member to affix a lower pulley and suspend the IV treatment bags or similar medications.

Yet still another object of the present invention is to provide an alternate adjustable and more secure bracket attachment.

Yet still another object of the present invention is to provide a method of utilizing the device that provides a unique means of positioning the bracket or hook attachments onto a desired structure, utilizing the pulley system to position the lower retaining member, suspending desired intravenous bags from the lower retaining member, and, safely administer IV medications to animals.

Further objects and advantages of the present invention will become apparent from a consideration of the drawings and ensuing description.

BRIEF DESCRIPTION OF THE DRAWINGS

The advantages and features of the present invention will become better understood with reference to the following more detailed description and claims taken in conjunction with the accompanying drawings in which like elements are identified with like symbols and in which:

FIG. 7 is a side perspective view of an upper bracket 41, according to a preferred embodiment of the present invention;

FIG. 8 is a top perspective view of the upper bracket 41, according to a preferred embodiment of the present invention;

FIG. 9 is a side perspective view of a lower bracket 45, according to a preferred embodiment of the present invention;

FIG. 10 is a top perspective view of the lower bracket 45, according to a preferred embodiment of the present invention;

FIG. 14 is a perspective view of a lower retaining member 60, according to a preferred embodiment of the present invention;

FIG. 15 is an opposing perspective view of the lower retaining member 60, according to a preferred embodiment of the present invention;

FIG. 19 is a top perspective view of an alternate upper bracket 80, according to a preferred embodiment of the present invention; and, FIG. 20 is a top perspective view of an alternate lower bracket 85, according to a preferred embodiment of the present invention.

Figure 1:
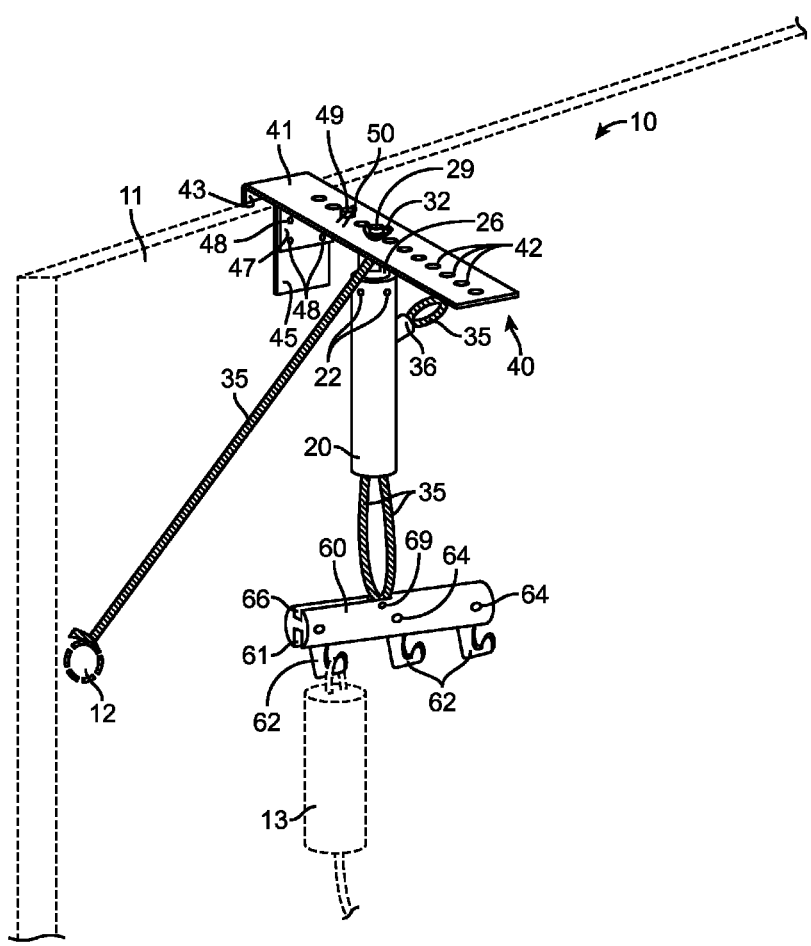
FIG. 1 is an environmental view of a portable IV hanger 10 depicting a bracket attachment 40, according to a preferred embodiment of the present invention.

DESCRIPTIVE KEY 10 portable IV hanger
11 structure
12 tie-off member
13 IV bag
14 conduit
20 upper retaining member
21 upper retaining member interior portion
22 pulley attachment aperture
23 cord aperture
24 upper pulley
25 upper pulley axle
26 pulley housing
27 pulley housing groove
28 housing aperture
29 stud
30 stud aperture
31 mechanical fastener
32 wing nut
35 cord
36 cord clamp
39 bracket gap
40 bracket attachment
41 upper bracket
42 upper bracket aperture
43 upper bracket brace
44 upper bracket fastener
45 lower bracket
46 lower bracket aperture
47 lower bracket brace
48 lower bracket fastener
49 lower bracket stud
50 cotter pin
55 hook attachment
56 hook
57 elongated nut fastener
60 lower retaining member
61 hook groove
62 retaining hook
63 retaining hook aperture
64 retaining hook fastening aperture
65 retaining hook axle
66 retaining member pulley groove
67 lower pulley
68 lower pulley aperture
69 lower pulley axle
70 lower pulley fastening aperture
80 alternate upper bracket
81 alternate upper bracket aperture
85 alternate lower bracket
86 alternate lower bracket aperture
87 alternate lower bracket stud

DETAILED DESCRIPTION OF THE PREFERRED EMBODIMENT

The best mode for carrying out the invention is presented in terms of its preferred embodiment, within FIGS. 1 through 18, and in terms of an alternate embodiment depicted within FIGS. 19 and 20. However, the invention is not limited to the described embodiment, and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a portable IV hanger (herein described as the "apparatus") 10, which provides a means to administer medications intravenously to large animals such as horses or the like. The apparatus 10 enables an IV bag 13 to be suspended in an adjustable manner which prohibits accidental toppling and enables an appropriate injection of the medication into the large animal.

Figure 2:
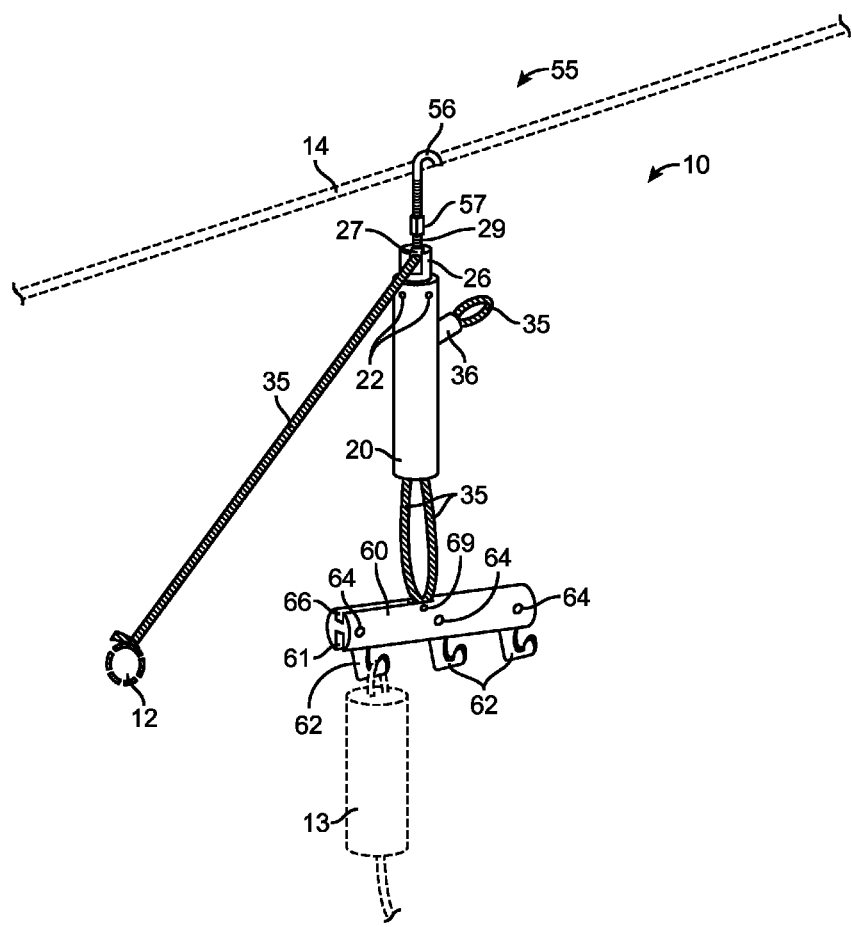
FIG. 2 is another environmental view of the portable IV hanger 10 depicting a hook attachment 55, according to a preferred embodiment of the present invention.

Referring now to FIG. 1, an environmental view of the apparatus 10 depicting a bracket attachment 40 and FIG. 2, another environmental view of the apparatus 10 depicting a hook attachment 55, according to the preferred embodiment of the present invention, are disclosed. The apparatus 10 comprises an upper retaining member 20 (also see FIGS. 3 and 4), an upper pulley 24 (see FIGS. 5 and 6), a lower retaining member 60 (also see FIGS. 14 through 16), and a lower pulley 67 (see FIG. 17). The upper retaining member 20 fixes the upper pulley 24 and enables a desired suspending means to suspend the apparatus 10. The apparatus 10 comprises a pair of suspending means which enables said apparatus 10 to be suspended from a structure 11 such as a stable wall or the like or a conduit 14 such as a water pipe as desired via a veterinarian or an animal handler. FIG. 1 depicts the suspending means as an adjustable bracket attachment 40 (also see FIGS. 7 through 12) which functions similarly to a common C-clamp and FIG. 2 depicts said suspending means as a hook attachment 55 (also see FIG. 13) which secures to a desired preferably horizontal fixed member. The lower retaining member 60 fixes the lower pulley 67 and suspends a desired amount of IV bags 13 which are routed to the large animal in a normal manner.

Figure 3:
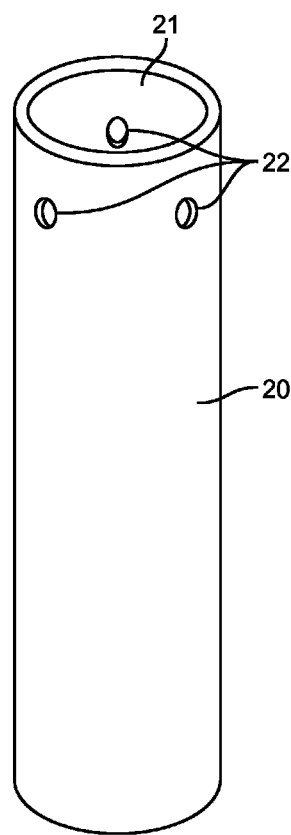
FIG. 3 is a perspective view of an upper retaining member 20, according to a preferred embodiment of the present invention.
Figure 4:
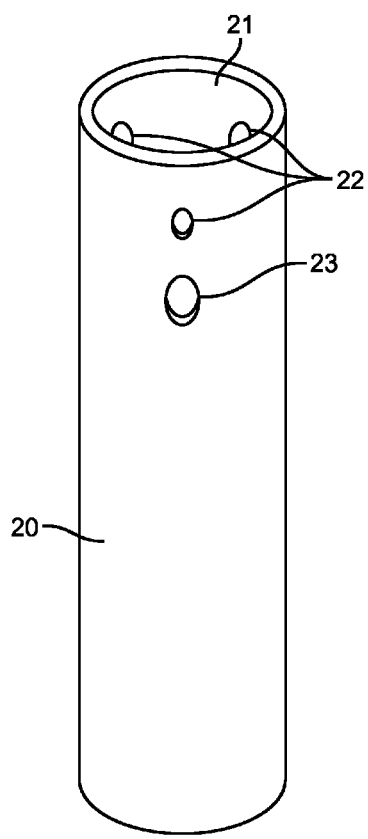
FIG. 4 is an opposing perspective view of the upper retaining member 20, according to a preferred embodiment of the present invention.
Figure 5:
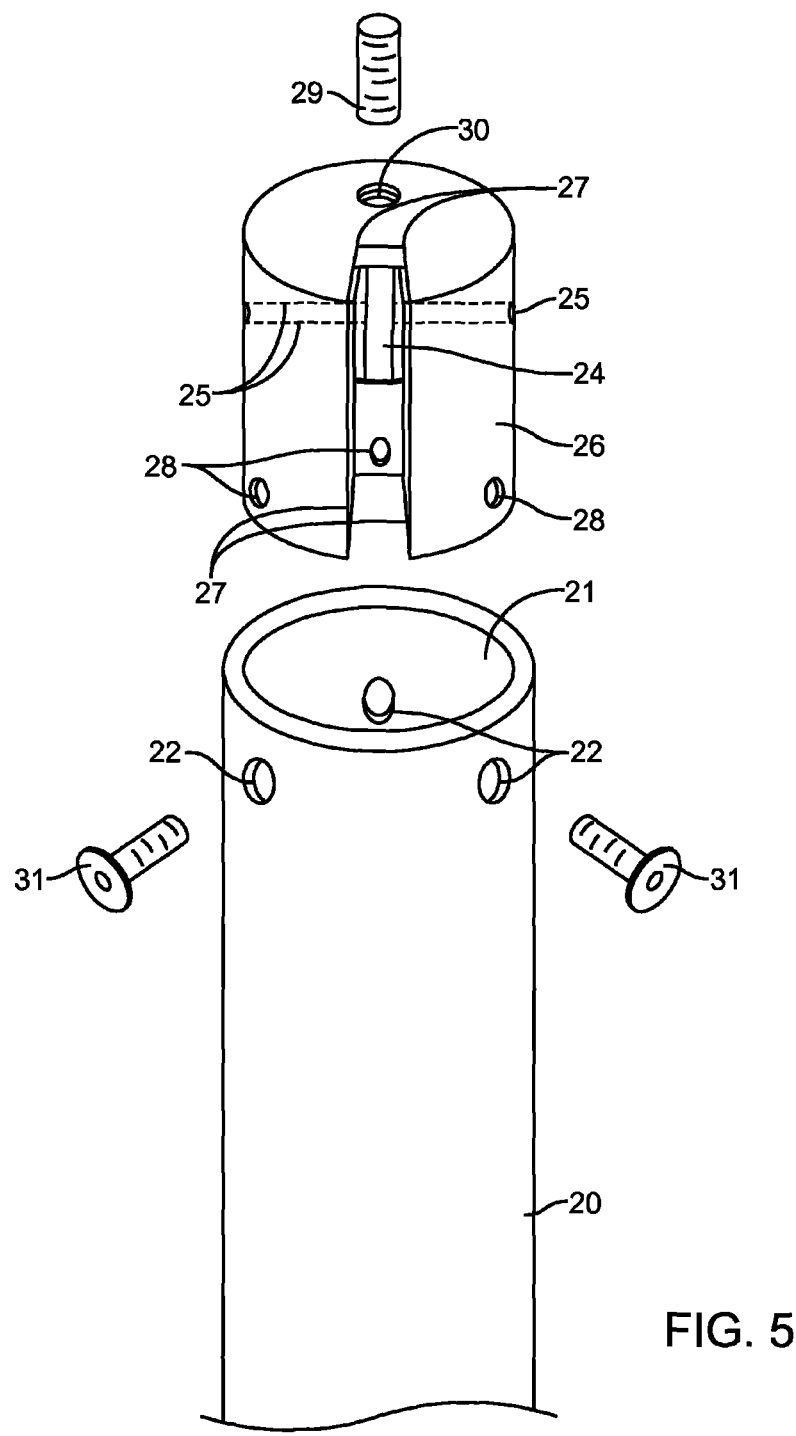
FIG. 5 is an exploded view of the upper retaining member 20 and an upper pulley 24, according to a preferred embodiment of the present invention.
Figure 6:
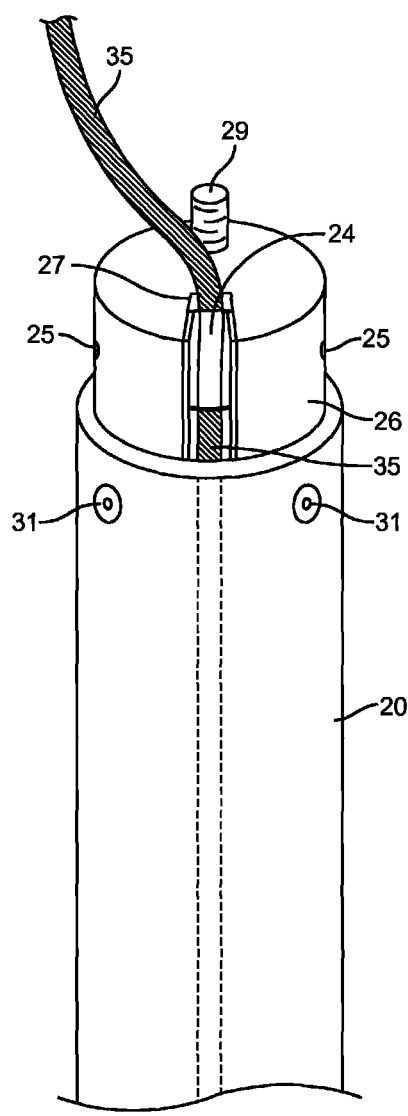
FIG. 6 is a perspective view of the upper retaining member 20 and the upper pulley 24, according to a preferred embodiment of the present invention.

Referring now to FIG. 3 through FIG. 6, various views of the upper retaining member 20, according to the preferred embodiment of the present invention, are disclosed. FIG. 3 depicts a perspective view of an upper retaining member 20, FIG. 4 depicts an opposing perspective view of the upper retaining member 20, FIG. 5 depicts an exploded view of the upper retaining member 20 and an upper pulley 24, and FIG. 6 depicts a perspective view of the upper retaining member 20 and the upper pulley 24. The upper retaining member 20 is preferably comprised of an elongated tube measuring approximately five-and-a-half (5½) inches in length and one-and-five-eighths (1⅝) inches in diameter, yet other shapes and dimensions may be utilized without limiting the scope of the apparatus 10. The upper retaining means 20 is fabricated from durable materials such as metal, plastic, or the like. The upper retaining member 20 is utilized to fix the upper pulley 24 (see herein below), route a cord 35, and retain the lower retaining member 60 for storage purposes (see FIG. 18).

A distal side surface of the upper retaining member 20 comprises a pair of pulley attachment apertures 22 which fasten a pulley housing 26 (see herein below) in a vertical position. An opposing side surface of the upper retaining member 20 also comprises another pulley attachment aperture 22 which also attaches to a rear portion of the pulley housing 26. Opposing the pulley attachment apertures 22 is a cord aperture 23 which enables a length of cord 35 to be clamped via a common cord clamp 36 (see FIGS. 1 and 2). The cord 35 is utilized to raise or lower the lower retaining member 60 via the pulleys 24, 67. As mentioned a distal end of the cord 35 is clamped via the cord clamp 36 which prohibits said cord 35 from becoming loose and secures said cord 35 to an external surface of the upper retaining member 20. A proximal end of the cord 35 is wrapped around a tie-off member 12 such as a door knob, handle, or the like after a desired the lower retaining member 60 has been set at a desired height (see FIGS. 1 and 2).

The upper pulley 24 is comprised of a disc-shaped device attached within a pulley housing groove 27 further within the pulley housing 26 via an upper pulley axle 25. The cord 35 runs over the upper pulley 24 and through an upper retaining member interior portion 21 to the lower pulley 67 to translate rotational motion to linear motion. The pulley housing 26 is depicted as a cylindrical member. The pulley housing groove 27 is positioned along an intermediate forward surface which extends vertically. The pulley housing groove 27 comprises a width and length which are slightly larger than the width and diameter of the upper pulley 27 accommodate placement. Each lower side of the pulley housing groove 27 and a lower rear surface of the pulley housing 26 comprises a housing aperture 28 which aligns with each respective pulley attachment aperture 22 upon the upper retaining member 20 to enable a mechanical fastener 31 such as a screw to be inserted for securing the pulley housing 26 to the upper retaining member interior portion 21. An upper rear surface of the pulley housing 26 comprises a threaded stud aperture 30 which enables a partial engaging of a threaded stud 29. The stud 29 extends from the stud aperture 30 to enable further attachment to the bracket attachment 40 or the hook attachment 55.

Figure 11:
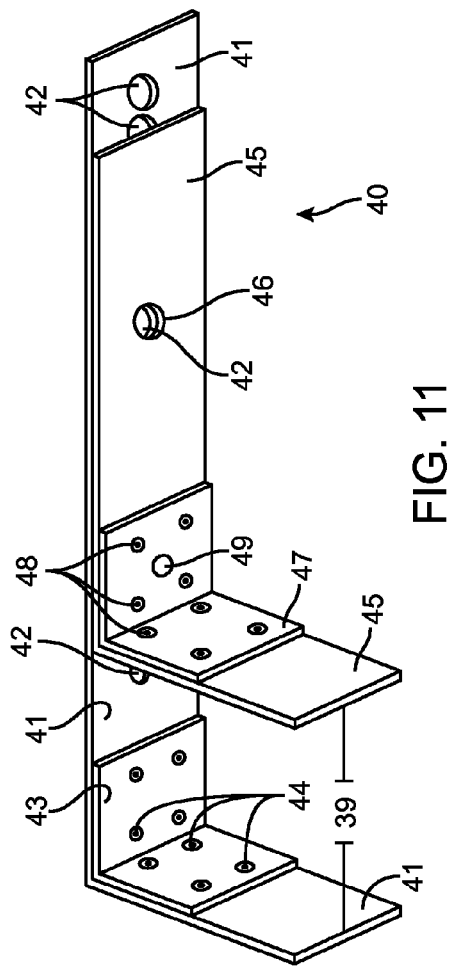
FIG. 11 is a side perspective view of the upper bracket 41 fastened to the lower bracket 45, according to a preferred embodiment of the present invention.
Figure 12:
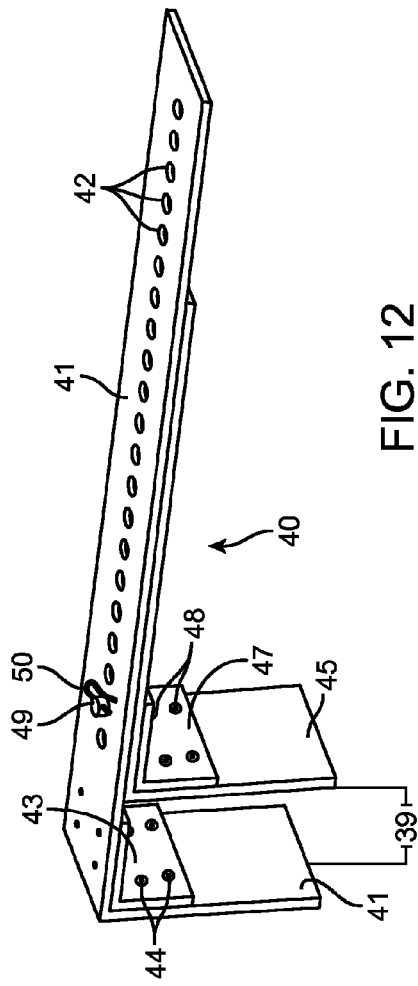
FIG. 12 is a top perspective view of the bracket attachment 40, showing the upper bracket 41 fastened to the lower bracket 45, according to a preferred embodiment of the present invention.

Referring now to FIG. 7 through FIG. 12, various views of the upper bracket 41, according to the preferred embodiment of the present invention, are disclosed. FIG. 7 depicts a side perspective view of the upper bracket 41, FIG. 8 depicts a top perspective view of the upper bracket 41, FIG. 9 depicts a side perspective view of the lower bracket 45, FIG. 10 depicts a top perspective view of the lower bracket 45, FIG. 11 depicts a side perspective view of the bracket attachment 40, and FIG. 12 depicts a top perspective view of the bracket attachment 40. The bracket attachment 40 comprises an upper bracket 41 and a lower bracket 45 which are adjustably fastened to create a bracket gap 39 which corresponds to the width of a desired structure 11 upon which the apparatus 10 is to be suspended. The bracket attachment 40 enables the upper retaining member 20 and lower retaining member 60 to be suspended from structures 11 such as, but not limited to: a stall wall, a door, or the like. The brackets 41, 45 are comprised of "L"-shaped members fabricated from aluminum, yet other materials may be utilized.

The upper bracket 41 comprises a plurality of parallel upper bracket apertures 42 along an intermediate surface of the lengthened portion of said upper bracket 41. The angled inner surface of the upper bracket 41 is reinforced with a shortened "L"-shaped upper bracket brace 43 which is attached to said upper bracket 41 with a plurality of upper bracket fasteners 44 which are comprised of rivets, screws, or the like. The upper bracket brace 43 strengthens the portion of the upper bracket 41 which undertakes the majority of the force created from the apparatus 10 against the desired structure 11.

The lower bracket 45 comprises a single lower bracket aperture 46 which is utilized to align to a desired upper bracket aperture 42 and enable insertion of the stud 29 upon the pulley housing 26. The stud 29 is fastened with a common wing nut 32 to an upper surface of the upper bracket 41. The angled inner surface of the lower bracket 45 is reinforced with a shortened "L"-shaped lower bracket brace 47 which is attached to said lower bracket 45 with a plurality of lower bracket fasteners 48 which are comprised of rivets, screws, or the like. The lower bracket brace 47 strengthens the portion of the lower bracket 45 which undertakes the majority of the force created from the apparatus 10 against the desired structure 11. An upper surface of the lengthened portion of the lower bracket 45 comprises a lower bracket stud 49 which is parallel to the lower bracket aperture 46. The lower bracket stud 49 is preferably threadably attached to the lower bracket 45 and lower bracket brace 47, yet other attachment means may be utilized such as welding without limiting the scope of the apparatus 10. The lower bracket stud 49 is inserted within another upper bracket aperture 42 which enables a common cotter pin 50 to be inserted through said lower bracket stud 49 to fasten the lower bracket 45 to the upper bracket 41. The positioning of the lower bracket stud 49 to the upper bracket aperture 42 determines the width of the bracket gap 39 which is further determined by the width of the desired structure 11 utilized to suspend the apparatus 10.

Figure 13:
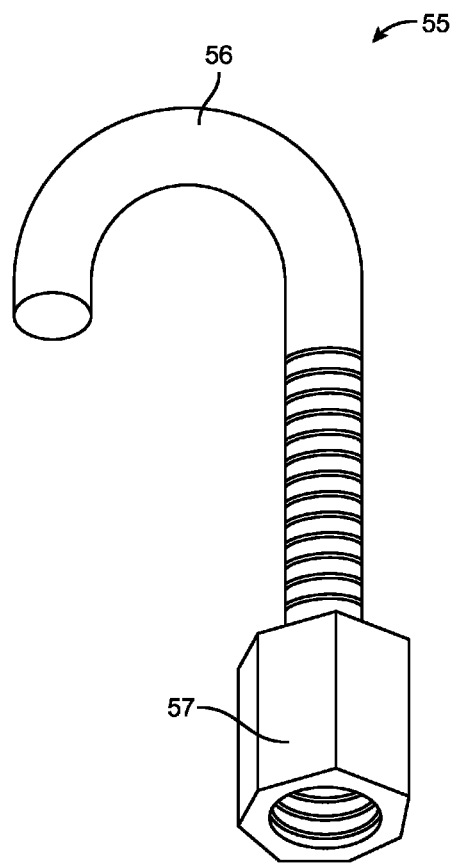
FIG. 13 is a perspective view of a hook attachment 55, according to a preferred embodiment of the present invention.

Referring now to FIG. 13, a perspective view of the hook attachment 55, according to the preferred embodiment of the present invention, is disclosed. The hook attachment 55 is utilized in lieu of the bracket attachment 55 and attaches to the stud 29 to enable the upper retaining member 20 and lower retaining member 60 to be suspended from conduits 14 such as, but not limited to: a water pipe, a bolt, another hook, or the like. The hook attachment 55 comprises a "J"-shaped threaded hook 56 and an elongated nut fastener 57. The hook 56 is suspended from a desired conduit 14 and the elongated nut fastener 57 is partially engaged upon a vertical portion of said hook 56 which enables said elongated nut fastener 57 to engage upon the stud 29. The hook attachment 55 is fabricated from materials such as, but not limited to: metal, plastic, or the like.

Figure 16:
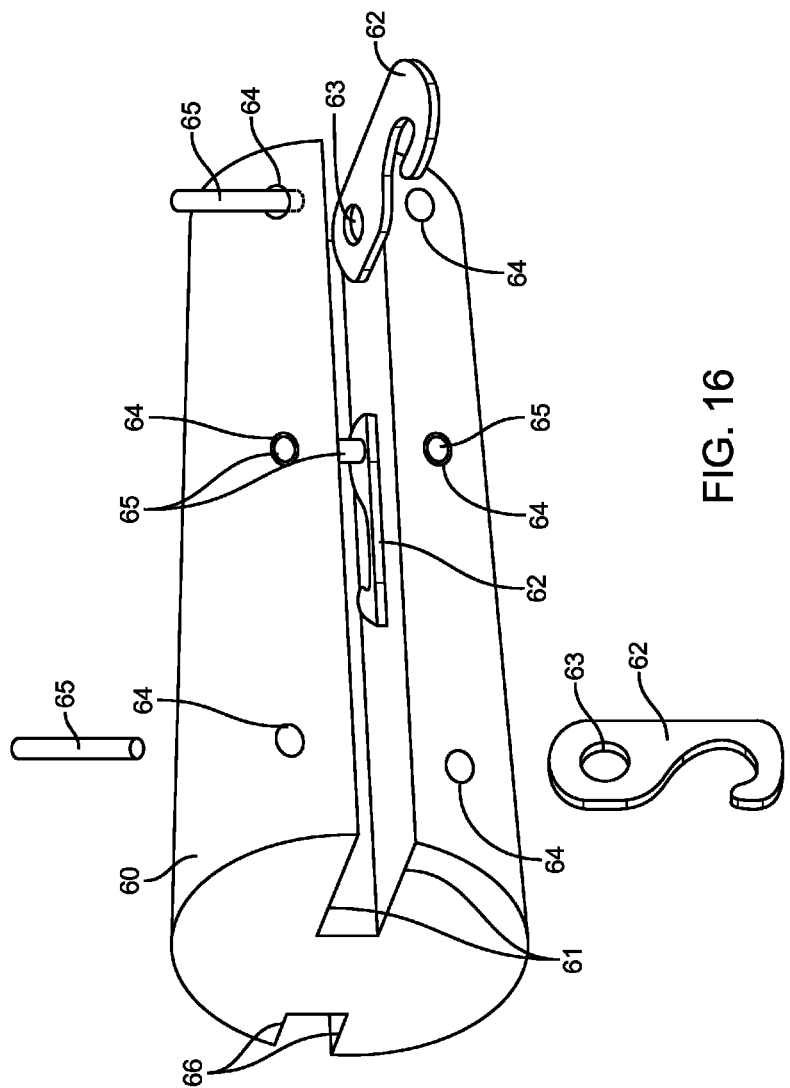
FIG. 16 is another perspective view of the lower retaining member 60 depicting a plurality of retaining hooks 62, according to a preferred embodiment of the present invention.
Figure 17:
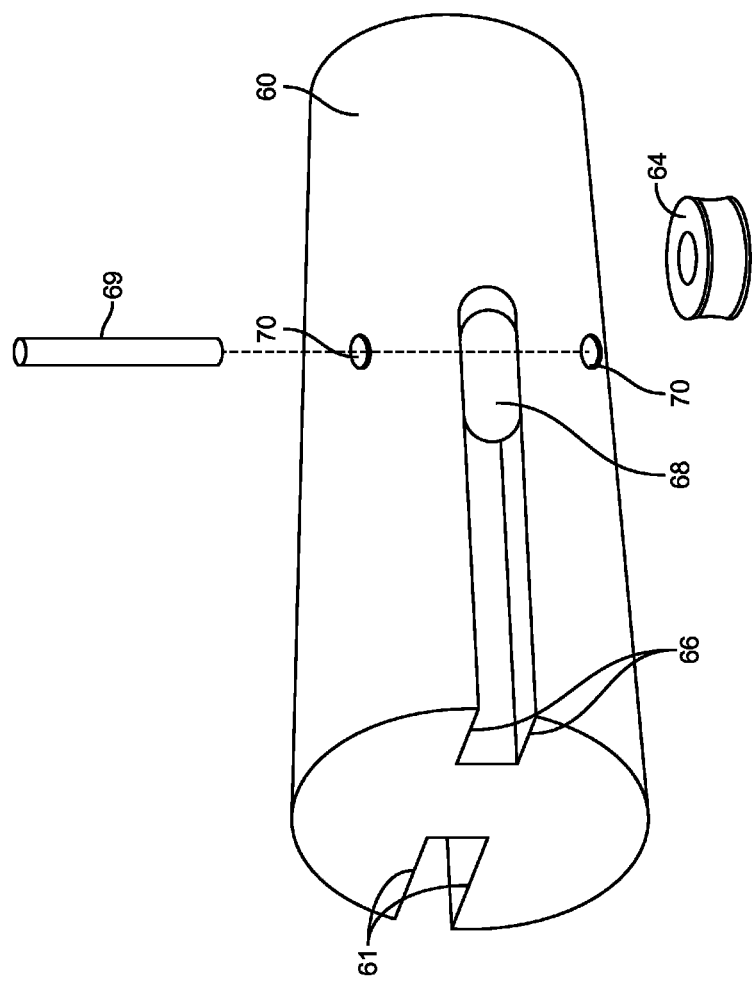
FIG. 17 is another opposing perspective view of the lower retaining member 60 depicting a lower pulley 67, according to a preferred embodiment of the present invention.

Referring now to FIG. 14, a perspective view of the lower retaining member 60, FIG. 15, is an opposing perspective view of the lower retaining member 60, FIG. 16, another perspective view of the lower retaining member 60 depicting a plurality of retaining hooks 62, and FIG. 17, another opposing perspective view of the lower retaining member 60 depicting a lower pulley 67, according to the preferred embodiment of the present invention, are disclosed. The lower retaining member 60 comprises a cylindrical shape measuring approximately five (5) inches in length and a one-and-a-half (1½) inches in diameter. The height adjustable lower retaining member 60 provides a means to suspend up to three (3) IV bags 13. The lower retaining member 60 is fabricated from materials similar to the upper retaining member 20.

A hook groove 61 is milled-out of a side surface of the lower retaining member 60 which preferably measures the entire length of said lower retaining member 60 and three-fourths (¾) of an inch in depth. The hook groove 61 enables up to three (3) retaining hooks 62 to be secured to the lower retaining member 60. Each retaining hook (see FIG. 16) comprises a "J"-shaped body further comprising a retaining hook aperture 63 upon an opposing portion. The retaining hook apertures 63 are positioned within the hook groove 61 and align with a respective retaining hook fastening aperture 64 which is located perpendicular to the hook groove 61. The retaining hook fastening apertures 64 enable insertion of a respective retaining hook axle 65 which fastens each retaining hook 62 and enables each said retaining hook 62 to pivot to a desired orientation. The retaining hooks 62 are pivoted within the hook groove 61 for storage purposes and pivoted out of said hook groove 61 for suspending IV bags 13.

Opposing the hook groove 61 is a retaining member pulley groove 66 which is utilized to mount the lower pulley 67. The retaining member pulley groove 66 is also milled-out of the lower retaining member 60 and extends half the length of the lower retaining member 60 and measures approximately one-fourth (¼) of an inch in depth. A lower pulley aperture 68 as a through hole between the hook groove 61 and an interior end portion of the retaining member pulley groove 66 enables the lower pulley 67 to be mounted within the retaining member pulley groove 66. The lower pulley 67 is similar to the upper pulley 24, yet redirects the cord 35 upwardly into the upper retaining member 20 and through the cord aperture 23 as abovementioned. The lower pulley 67 is fastened within the retaining member pulley groove 66 via inserting a lower pulley axle 69 though each lower pulley fastening aperture 70. The upper pulley 24 in conjunction with the lower pulley 67 lifts the lower retaining member 60 to a desired height as to not interfere with the animal.

Figure 18:
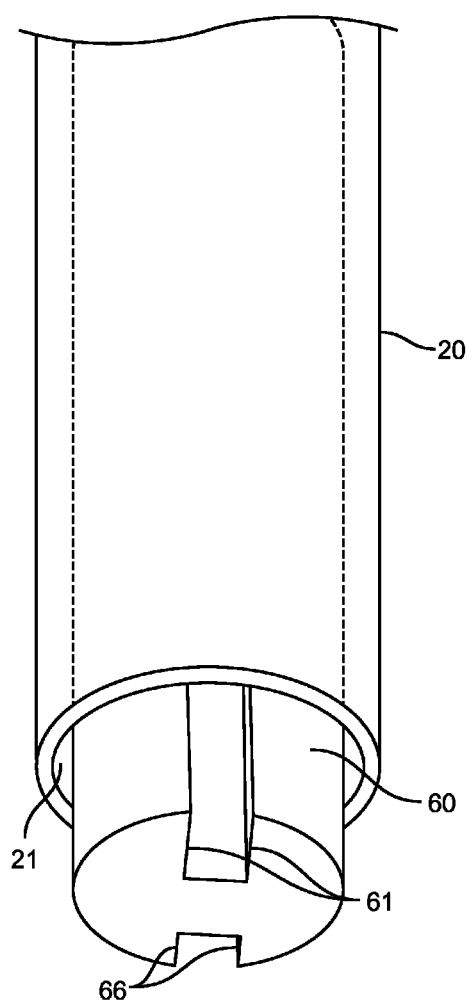
FIG. 18 is a perspective view of the lower retaining member 60 stored within the upper retaining member 20, according to a preferred embodiment of the present invention.

Referring now to FIG. 18, a perspective view of the lower retaining member 60 stored within the upper retaining member 20, according to the preferred embodiment of the present invention, is disclosed. In storage situations, the lower retaining member 60 is slid within the upper retaining member interior portion 21 that which opposes the pulley housing 26. Each retaining hook 62 is pivoted within the hook groove 61 before the lower retaining member 60 is positioned within the upper retaining member 20.

Referring now to FIG. 19, a top perspective view of the alternate upper bracket 80 and FIG. 20, a top perspective view of the alternate lower bracket 85, according to the preferred embodiment of the present invention, are disclosed. The apparatus 10 also comprises an alternate upper bracket 80 and an alternate lower bracket 85 which are comprised of "L"-shaped members and fabricated from a strong and durable material such as steel to provide additional support. The usage of a stronger material enables the abovementioned bracket braces 43, 47 to be eliminated. The alternate upper bracket 80 comprises a plurality of parallel alternate upper bracket apertures 81. The upper bracket apertures 81 align with an alternate lower bracket aperture 86 and an alternate lower bracket stud 87 which is secured with a cotter pin 50 similar as the abovementioned. The alternate brackets 80, 85 function similar to the abovementioned bracket attachment 40.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the apparatus 10, it would be installed as indicated in FIGS. 1 and 2.

The method of installing and utilizing the apparatus 10 with the bracket attachment 40 may be achieved by performing the following steps: acquiring the apparatus 10; inserting the lower bracket stud 49, 87 within a desired upper bracket aperture 42, 81 to construct a desired bracket gap 39; inserting the cotter pin 50 within the lower bracket stud 49, 87; inserting the stud 29 within the lower bracket aperture 46, 86 and aligned bracket aperture 42, 81 and engaging the wing nut 32 onto said stud 29; positioning the bracket attachment 40 upon a desired structure 11; pulling the cord 35 to enable said cord 35 to run along each pulley 24, 67 to position the lower retaining member 60 to a desired height and wrapping the end portion of said cord 35 onto a desired tie-off member 12; utilizing the retaining hooks 62 to suspend a desired IV bag(s) 13; utilizing the apparatus 10 as necessary; removing the IV bag(s) 13 as desired; unwrapping the cord 35 from the tie-off member 12; removing the bracket attachment 40 from the desired structure 11 as necessary; storing the lower retaining member 60 within the upper retaining member 20 as needed; and, providing means to safely administer IV medications to large animals in a manner which is quick, easy, and effective.

The method of installing and utilizing the apparatus 10 with the hook attachment 55 may be achieved by performing the following steps: acquiring the apparatus 10; threadably attaching the elongated nut fastener 57 onto the stud 29; suspending the hook 56 to a desired section of conduit 14; pulling the cord 35 to enable said cord 35 to run along each pulley 24, 67 to position the lower retaining member 60 to a desired height and wrapping the end portion of said cord 35 onto a desired tie-off member 12; utilizing the retaining hooks 62 to suspend a desired IV bag(s) 13; utilizing the apparatus 10 as necessary; removing the IV bag(s) 13 as desired; unwrapping the cord 35 from the tie-off member 12; removing the hook attachment 55 from the desired conduit 14 as necessary; storing the lower retaining member 60 within the upper retaining member 20 as needed; and, providing means to safely administer IV medications to large animals in a manner which is quick, easy, and effective.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A portable hanger adapted for suspending at least one IV bag, comprising:
   an upper retaining member, comprising:
      an elongated hollow tube having an upper end and a lower end;
      a pair of first upper pulley attachment apertures located adjacent to an upper perimeter edge of a first side said tube upper end;
      a second upper pulley attachment aperture located opposite a centerline of said pair of first upper pulley attachment apertures adjacent to an upper perimeter edge of a second side of said tube upper end; and, a cord aperture located subjacent to said second upper pulley attachment aperture;
an upper pulley assembly retained in said tube upper end and secured thereto via a desired one of said pulley attachment apertures;
an upper suspension means removably attached to said upper retaining member;
a lower retaining member;
a lower pulley assembly affixed to said lower retaining member; and,
a cord, routed through said cord aperture, said upper retaining member, said lower retaining member, and said lower pulley assembly, and having a cord clamp located at a first end such that said cord clamp restricts said cord first end from traveling through said cord aperture;
wherein said upper suspension means removably suspends said hanger from a support structure;
wherein said lower retaining member is sized and shaped so as to be retained within said upper retaining member within a storage configuration;
wherein said lower retaining member is adapted to suspend said at least one IV bag in a manner which prohibits accidental toppling; and
wherein said cord vertically motions said lower retaining member relative to said upper retaining member.

2. The hanger of claim 1, wherein said upper pulley assembly further comprises:
an upper pulley housing, comprising a cylindrical member sized to be inserted within said tube upper end of said upper retaining member, further comprising:
an upper pulley groove located at a first side thereof and longitudinally spanning from a perimeter upper edge to a perimeter bottom edge;
a pair of first upper pulley housing apertures located adjacent to said upper pulley housing perimeter bottom edge;
a second upper pulley housing aperture located opposite a centerline of said pair of first upper pulley housing apertures adjacent to said upper pulley housing perimeter bottom edge; and,
a threaded stud aperture located at an upper rear surface of said upper pulley housing; and,
a disc-shaped upper pulley, comprising an upper pulley axle attached to side walls of said groove of said upper pulley housing;
wherein said upper pulley fully resides within said upper pulley groove of said upper pulley housing;
wherein said cord is routed between said upper pulley and an inner wall of said upper pulley groove of said upper pulley housing;
wherein a fastening means secures said pair of first upper pulley housing apertures to said pair of first upper pulley attachment apertures and another fastening means secures said second upper pulley housing aperture to said second upper pulley attachment aperture; and,
wherein said threaded stud apertures threadably engages said upper suspension means.

3. The hanger of claim 1, wherein said upper suspension means further comprises an adjustable bracket attachment assembly, further comprising:
an upper bracket, comprising an "L"-shaped angle member wherein an elongated planar portion comprises plurality of upper bracket apertures; and,
a lower bracket, comprising an "L"-shaped angle member wherein an elongated portion comprises a lower bracket aperture and a lower bracket stud fastened to and outwardly extending from an outer surface thereof;
wherein said lower bracket aperture is aligned with a desired one of said plurality of upper bracket apertures and affixed therethrough with a fastener to said upper pulley assembly;
wherein said lower bracket stud and said lower bracket aperture are horizontally aligned;
wherein said lower bracket stud is correspondingly inserted within another desired one of said plurality of upper bracket apertures and secured with a fastener to determine a width of a bracket gap; and,
wherein said bracket gap is adapted to correspond to a width of said support structure.

4. The hanger of claim 3, wherein said upper suspension means further comprises:
an upper bracket brace, comprising an "L"-shaped brace member fastened to a corner portion of said upper bracket; and,
a lower bracket brace, comprising an "L"-shaped brace member fastened to a corner portion of said lower bracket.

5. The hanger of claim 1, wherein said lower retaining member further comprises:
an elongated tube having an first end and a second end;
a hook groove located at a first side thereof and longitudinally spanning from perimeter edges of said first side and said second side;
a plurality of aligned pairs of IV bag retaining apertures on opposite sides of said hook groove;
a lower pulley groove located at a second side of opposite of said hook groove and extending from a perimeter edge of said first side to an intermediate point;
a lower pulley aperture located at an interior end of said lower pulley groove and extending through to said hook groove; and,
a pair of aligned lower pulley fastening apertures locate on opposite sides of said lower pullet groove;
wherein an IV bag suspension means is removably inserted and secure to one of said pairs of IV bag retaining apertures; and,
wherein said lower pulley assembly is retained therein said lower pulley aperture of said lower pulley groove and secured thereto via said pair of lower pulley fastening apertures.

6. The hanger of claim 5, wherein said IV bag suspension means further comprises:
a generally "J"-shaped retaining hook body having an IV hook end and a retaining hook aperture; and,
a retaining hook axle;
wherein said hook body is inserted within said hook groove such that said retaining hook aperture is aligned with a desired one of said pairs of IV bag retaining apertures; and,
wherein said retaining hook axle is routed through said desired pairs of said plurality of IV bag retaining apertures and said retaining hook aperture.

7. The hanger of claim 5, wherein said lower pulley assembly further comprises:
a disc-shaped lower pulley; and,
a lower pulley axle;
wherein said lower pulley axle is removably inserted into said pair of lower pulley fastening apertures and said lower pulley to secure said lower pulley to said lower retaining member; and,
wherein said cord is routed between said lower pulley and an inner wall of said lower pulley groove of said lower retaining member.

8. The hanger of claim 1, wherein:
said upper retaining member is approximately five-and-a-half inches in length and one-and-five-eighths inches in diameter; and,
said lower retaining member is approximately five inches in length and a one-and-a-half inches in diameter.

9. A portable hanger, comprising:
an upper retaining member, comprising:
an elongated hollow tube having an upper end and a lower end;
a pair of first upper pulley attachment apertures located adjacent to an upper perimeter edge of a first side said tube upper end;
a second upper pulley attachment aperture located opposite a centerline of said pair of first upper pulley attachment apertures adjacent to an upper perimeter edge of a second side of said tube upper end; and,
a cord aperture located subjacent to said second upper pulley attachment aperture;
an upper pulley assembly retained in said tube upper end and secured thereto via a desired one of said pulley attachment apertures;
an upper suspension means removably attached to said upper retaining member;
a lower retaining member;
a lower pulley assembly affixed to said lower retaining member;
a cord, routed through said cord aperture, said upper retaining member, said lower retaining member, and said lower pulley assembly, and having a cord clamp located at a first end such that said cord clamp restricts said cord first end from traveling through said cord aperture; and,
at least one IV bag;
wherein said upper suspension means removably suspends said hanger from a support structure;
wherein said lower retaining member is sized and shaped so as to be retained within said upper retaining member within a storage configuration;
wherein said lower retaining member is adapted to suspend said at least one IV bag in a manner which prohibits accidental toppling;
wherein said cord vertically motions said lower retaining member relative to said upper retaining member; and,
wherein said hanger enables an appropriate injection of a medication within said at least one IV bag into a subject.

10. The hanger of claim 9, wherein said upper pulley assembly further comprises:
an upper pulley housing, comprising a cylindrical member sized to be inserted within said tube upper end of said upper retaining member, further comprising:
an upper pulley groove located at a first side thereof and longitudinally spanning from a perimeter upper edge to a perimeter bottom edge;
a pair of first upper pulley housing apertures located adjacent to said upper pulley housing perimeter bottom edge;
a second upper pulley housing aperture located opposite a centerline of said pair of first upper pulley housing apertures adjacent to said upper pulley housing perimeter bottom edge; and,
a threaded stud aperture located at an upper rear surface of said upper pulley housing; and,
a disc-shaped upper pulley, comprising an upper pulley axle attached to side walls of said groove of said upper pulley housing;
wherein said upper pulley fully resides within said upper pulley groove of said upper pulley housing;
wherein said cord is routed between said upper pulley and an inner wall of said upper pulley groove of said upper pulley housing;
wherein a fastening means secures said pair of first upper pulley housing apertures to said pair of first upper pulley attachment apertures and another fastening means secures said second upper pulley housing aperture to said second upper pulley attachment aperture; and,
wherein said threaded stud apertures threadably engages said upper suspension means.

11. The hanger of claim 9, wherein said upper suspension means further comprises an adjustable bracket attachment assembly, further comprising:
an upper bracket, comprising an "L"-shaped angle member wherein an elongated planar portion comprises plurality of upper bracket apertures; and,
a lower bracket, comprising an "L"-shaped angle member wherein an elongated portion comprises a lower bracket aperture and a lower bracket stud fastened to and outwardly extending from an outer surface thereof;
wherein said lower bracket aperture is aligned with a desired one of said plurality of upper bracket apertures and affixed therethrough with a fastener to said upper pulley assembly;
wherein said lower bracket stud and said lower bracket aperture are horizontally aligned;
wherein said lower bracket stud is correspondingly inserted within another desired one of said plurality of upper bracket apertures and secured with a fastener to determine a width of a bracket gap; and,
wherein said bracket gap is adapted to correspond to a width of said support structure.

12. The hanger of claim 11, wherein said upper suspension means further comprises:
an upper bracket brace, comprising an "L"-shaped brace member fastened to a corner portion of said upper bracket; and,
a lower bracket brace, comprising an "L"-shaped brace member fastened to a corner portion of said lower bracket.

13. The hanger of claim 9, wherein said lower retaining member further comprises:
an elongated tube having an first end and a second end;
a hook groove located at a first side thereof and longitudinally spanning from perimeter edges of said first side and said second side;
a plurality of aligned pairs of IV bag retaining apertures on opposite sides of said hook groove;
a lower pulley groove located at a second side of opposite of said hook groove and extending from a perimeter edge of said first side to an intermediate point;
a lower pulley aperture located at an interior end of said lower pulley groove and extending through to said hook groove; and,
a pair of aligned lower pulley fastening apertures locate on opposite sides of said lower pullet groove;
wherein an IV bag suspension means is removably inserted and secure to one of said pairs of IV bag retaining apertures; and,
wherein said lower pulley assembly is retained therein said lower pulley aperture of said lower pulley groove and secured thereto via said pair of lower pulley fastening apertures.

14. The hanger of claim 13, wherein said IV bag suspension means further comprises:
- a generally "J"-shaped retaining hook body having an IV hook end and a retaining hook aperture; and,
- a retaining hook axle;
- wherein said hook body is inserted within said hook groove such that said retaining hook aperture is aligned with a desired one of said pairs of IV bag retaining apertures; and,
- wherein said retaining hook axle is routed through said desired pairs of said plurality of IV bag retaining apertures and said retaining hook aperture.

15. The hanger of claim 13, wherein said lower pulley assembly further comprises:
- a disc-shaped lower pulley; and,
- a lower pulley axle;
- wherein said lower pulley axle is removably inserted into said pair of lower pulley fastening apertures and said lower pulley to secure said lower pulley to said lower retaining member; and,
- wherein said cord is routed between said lower pulley and an inner wall of said lower pulley groove of said lower retaining member.

16. The hanger of claim 9, wherein:
- said upper retaining member is approximately five-and-a-half inches in length and one-and-five-eighths inches in diameter; and, said lower retaining member is approximately five inches in length and a one-and-a-half inches in diameter.

* * * * *